US011123276B2

(12) United States Patent
Liang et al.

(10) Patent No.: US 11,123,276 B2
(45) Date of Patent: Sep. 21, 2021

(54) COSMETIC COMPOSITIONS

(71) Applicant: L'Oreal, Paris (FR)

(72) Inventors: Jun Liang, Staten Island, NY (US); Heather Lee, Wayne, NJ (US); Angela Park, Jersey City, NJ (US)

(73) Assignee: L'OREAL, Paris (FR)

(*) Notice: Subject to any disclaimer, the term of this patent is extended or adjusted under 35 U.S.C. 154(b) by 330 days.

(21) Appl. No.: 15/907,784

(22) Filed: Feb. 28, 2018

(65) Prior Publication Data
US 2019/0262246 A1 Aug. 29, 2019

(51) Int. Cl.
A61Q 5/02 (2006.01)
A61K 8/44 (2006.01)
A61K 8/37 (2006.01)
A61K 8/60 (2006.01)
A61Q 19/10 (2006.01)

(52) U.S. Cl.
CPC ............. A61K 8/44 (2013.01); A61K 8/375 (2013.01); A61K 8/602 (2013.01); A61K 8/604 (2013.01); A61Q 5/02 (2013.01); A61Q 19/10 (2013.01); A61K 2800/30 (2013.01); A61K 2800/33 (2013.01)

(58) Field of Classification Search
None
See application file for complete search history.

(56) References Cited

U.S. PATENT DOCUMENTS

| | | | |
|---|---|---|---|
| 4,292,426 A | 9/1981 | Orii et al. | |
| 8,193,137 B2 | 6/2012 | Kunieda et al. | |
| 8,518,991 B2 | 8/2013 | Gunn et al. | |
| 10,265,261 B2 | 4/2019 | Park et al. | |
| 2003/0059382 A1 | 3/2003 | Brandt et al. | |
| 2004/0156805 A1 | 8/2004 | Kazmi et al. | |
| 2009/0181060 A1 | 7/2009 | Rosato et al. | |
| 2009/0185989 A1 | 7/2009 | Golz-Berner et al. | |
| 2009/0270297 A1 | 10/2009 | Luciow et al. | |
| 2009/0305929 A1 | 12/2009 | Luciow et al. | |
| 2010/0280111 A1* | 11/2010 | Aoki | A61K 8/44 514/547 |
| 2014/0186284 A1 | 7/2014 | Sha et al. | |
| 2014/0349902 A1 | 11/2014 | Allef et al. | |
| 2015/0297489 A1 | 10/2015 | Kleinen et al. | |
| 2016/0120803 A1* | 5/2016 | Mathur | A61Q 19/00 514/169 |
| 2016/0296448 A1 | 10/2016 | Terrisse et al. | |
| 2017/0000713 A1* | 1/2017 | Bakes | A61K 8/35 |
| 2017/0071835 A1 | 3/2017 | Schelges et al. | |
| 2017/0079898 A1 | 3/2017 | Fevola et al. | |
| 2017/0239155 A1 | 8/2017 | Hartnett et al. | |
| 2017/0333332 A1 | 11/2017 | Jia et al. | |
| 2018/0116937 A1 | 5/2018 | Park et al. | |
| 2018/0168945 A1 | 6/2018 | Schoepgens et al. | |
| 2019/0125650 A1 | 5/2019 | Lee et al. | |
| 2020/0170894 A1 | 6/2020 | Park et al. | |
| 2020/0276099 A1 | 9/2020 | Robbins et al. | |

FOREIGN PATENT DOCUMENTS

| | | |
|---|---|---|
| DE | 10044662 A1 | 3/2002 |
| DE | 10 2006 008920 B3 | 8/2007 |
| DE | 20 2015 005 287 U1 | 10/2015 |
| EP | 1716842 A2 | 11/2006 |
| EP | 2335681 A1 | 6/2011 |
| EP | 2505180 A1 | 10/2012 |
| EP | 2532343 A1 | 12/2012 |
| EP | 3006088 A1 | 4/2016 |
| FR | 3018044 A1 | 9/2015 |
| WO | 2016/079007 A1 | 5/2016 |
| WO | 2016/079008 A1 | 5/2016 |
| WO | 2016/079009 A1 | 5/2016 |
| WO | 2017/099559 A1 | 6/2017 |
| WO | 2017/106276 A1 | 6/2017 |
| WO | 2018/002557 A1 | 1/2018 |
| WO | 2019/000394 A1 | 1/2019 |

OTHER PUBLICATIONS

International Search Report and Written Opinion for Application No. PCT/US2019/019748, dated Apr. 23, 2019.
Non-Final Office Action for copending U.S. Appl. No. 15/799,229, dated Oct. 6, 2020.
Mintel: "Shampoo," Mintel.com, Sep. 13, 2016. pp. 1-6.
Non-Final Office Action for copending U.S. Appl. No. 15/799,229, dated May 6, 2019.
Final Office Action for copending U.S. Appl. No. 15/799,229, dated Mar. 20, 2020.
Non-Final Office Action for copending U.S. Appl. No. 16/204,591, dated Sep. 23, 2020.
"Jason Shampoo and Conditioner" web product page (Oct. 9, 2016), Obtained from <https://www.burpy.com/whole-foods/jason-dandruff-relief-2-in-1-shampoo-conditioner-treatment/product-detail/1367207.
Mintel: "Gentle Conditioning Shampoo," Caudalie, Record ID 3537355, published Nov. 2015, pp. 1-2.
Mintel: "Anti-Dandruff Shampoo," Melvita, Record ID 298774, published Sep. 2004, pp. 1-2.
Mintel: "Exfoliating Scalp Shampoo," Kanellia, Record ID 3384671, published Oct. 2015, pp. 1-2.
Mintel: "Charcoal + Coconut Oil Micro-Exfoliating Shampoo," Briogeo Scalp Revival, Record ID 4787991, published Jun. 2017, pp. 1-5.

(Continued)

Primary Examiner — Nissa M Westerberg
(74) Attorney, Agent, or Firm — The Marbury Law Group, PLLC

(57) ABSTRACT

The present disclosure relates to compositions and methods for treating and/or cleansing keratinous materials. The compositions comprise at least one carboxylate anionic surfactant, at least one secondary surfactant other than the at least one carboxylate anionic surfactant, at least one glyceryl ester, and a cosmetically acceptable solvent, wherein the at least one carboxylate anionic surfactant and the at least one glyceryl ester are present in a weight ratio ranging from about 0.50 to about 1.00.

24 Claims, No Drawings

(56) References Cited

OTHER PUBLICATIONS

International Search Report and Written Opinion for counterpart Application No. PCT/US2020/019408, dated May 14, 2020.
Mintel: "Pureness Shampoo," Biopoint, XP055692070, Aug. 8, 2018.
Non-Final Office Action for copending U.S. Appl. No. 16/796,865, dated Dec. 8, 2020.
Song et al., "Homogeneous Quaternization of Cellulose in NaOH/Urea Aqueous Solutions as Gene Carriers," Biomacromolecules, 2008, 9, pp. 2259-2264.
Lamesoft® PO 65 Data Profile, carechemicals, 2007, Revision 14—Jul. 2007.
Final Office Action for copending U.S. Appl. No. 16/204,591, dated May 3, 2021.
Final Office Action for copending U.S. Appl. No. 16/796,865, dated May 21, 2021.

* cited by examiner

COSMETIC COMPOSITIONS

FIELD OF THE INVENTION

The disclosure relates to cosmetic compositions, such as shampoos, body cleansers, and face cleansers, for treating and/or cleansing keratinous materials and to methods of cleansing keratinous materials.

BACKGROUND

Consumers desire compositions for applying to and/or cleansing keratinous materials, including hair and skin. Such compositions require a certain viscosity or rheology to be recognized as a specific product—e.g., a shampoo, a body cleanser, or a face cleanser—and to be convenient for dispensing and using and thus desirable to consumers. It is known practice to use compositions that contain conventional thickeners, either natural or synthetic, in order to give such compositions a certain viscosity or rheology. Nonetheless, chemicals and raw materials used in cleansing compositions, including conventional thickeners, may lack sustainable sourcing and not comply with "green" manufacturing processes, which in turn can lead to harmful effects on the environment.

Consumers also desire cleansing compositions that adequately cleanse the hair and/or skin, without leaving undesirable amounts of coating and/or residue on the hair and/or skin. Coating and/or residue left on the hair and/or skin is usually attributable to conventional thickeners, including sclerotium gum.

It is also desirable for consumers to use cleansing compositions that produce adequate foam in addition to also being sulfate-free.

Due to the concerns regarding conventional thickeners and/or sulfate-containing surfactants, manufacturers seek to formulate compositions for applying to and/or cleansing keratinous materials using ingredients and combinations of ingredients that can minimize or prevent the above-described disadvantages. However, the choice of ingredients or combinations of ingredients could pose difficulties insofar as they cannot be detrimental to other cosmetic attributes such as cosmetic feel, volume, bounce, hair individualization, and suppleness; viscosity or rheology properties of cleansing compositions; stability of the compositions, or result in more disadvantages such as increased irritation of the scalp and damage to the hair. It is therefore desirable to provide the consumer with compositions that can care for and/or cleanse keratinous materials, wherein the compositions have the desired viscosity or rheology and cosmetic attributes, while being comprised of raw materials that are of sustainable sourcing and produced by green manufacturing processes. It is also desirable to provide consumers with compositions that are sulfate-free.

The disclosed embodiments provide compositions for applying to and/or cleansing keratinous materials.

It has now been surprisingly and unexpectedly discovered that combining at least one carboxylate anionic surfactant, at least one secondary surfactant other than the at least one carboxylate anionic surfactant, at least one glyceryl ester, and a cosmetically acceptable solvent, wherein the at least one carboxylate anionic surfactant and the at least one glyceryl ester are present in a weight ratio ranging from about 0.50 to about 1.00, results in compositions with the desired level of viscosity or rheology, without using conventional thickeners (e.g., without using synthetic associative thickeners and/or thickening polymers). Such compositions also provide an acceptable level of cosmetic attributes to the keratinous materials, such as cleaner feel to the hair, with less coating and deposition. The compositions also provide adequate foaming while being sulfate-free.

SUMMARY

The disclosure relates, in various embodiments, to compositions comprising at least one carboxylate anionic surfactant, at least one secondary surfactant other than the at least one carboxylate anionic surfactant, at least one glyceryl ester, and a cosmetically acceptable solvent, wherein the at least one carboxylate anionic surfactant and the at least one glyceryl ester are present in a weight ratio ranging from about 0.50 to about 1.00.

In further embodiments, the at least one carboxylate anionic surfactant in the compositions is chosen from acylglycinates, acylsarcosinates, acyllactylates, acylglutamates, alkyl ether carboxylates, or mixtures thereof.

In further embodiments, the at least one carboxylated anionic surfactant is chosen from stearoylglutamates, lauroylglutamates, cocoylglutamates, sodium cocoyl glutamate, disodium cocoyl glutamate, lauryl ether carboxylates, myristoyl glutamate, olivoyl glutamate, capryloyl glutamate, palm itoylsarcosinates, stearoylsarcosinates, lauroylsarcosinates, cocoylacyllactylates, behenoyllactylates, lauroyllactylates, (iso)stearoyllactylates, salts thereof, or mixtures thereof.

In further embodiments, the at least one carboxylate anionic surfactant is chosen from disodium cocoyl glutamate, sodium cocoyl glutamate, or mixtures thereof.

In further embodiments, the at least one carboxylate anionic surfactant is present in a total amount ranging from about 0.1% to about 10% by weight, relative to the total weight of the composition.

In further embodiments, the at least one carboxylate anionic surfactant is present in a total amount ranging from about 1% to about 3% by weight, relative to the total weight of the composition.

In further embodiments, the at least one secondary surfactant is chosen from non-carboxylate anionic surfactants, amphoteric/zwitterionic surfactants, nonionic surfactants, or mixtures thereof.

In further embodiments, the at least one secondary surfactant is present in a total amount ranging from about 0.1% to about 25% by weight, relative to the total weight of the composition In further embodiments, the at least one secondary surfactant is present in a total amount ranging from about 3% to about 18% by weight, relative to the total weight of the composition.

In further embodiments, the at least one secondary surfactant includes nonionic surfactants chosen from alkylpolyglycosides (alkylpolyglucosides), for example, lauryl glucoside, decyl glucoside, coco-glucoside, or mixtures thereof.

In further embodiments, the at least one secondary surfactant is chosen from nonionic surfactants, wherein the at least one nonionic surfactant is present in a total amount ranging from about 0.1% to about 20% by weight, relative to the total weight of the composition.

In further embodiments, the at least one secondary surfactant is chosen from nonionic surfactants, and the at least one nonionic surfactant is present in a total amount ranging from about 8% to about 12% by weight, relative to the total weight of the composition.

In further embodiments, the at least one secondary surfactant is chosen from amphoteric/zwitterionic surfactants chosen from betaines, sultaines, amphoacetates, amphoproprionates, or mixtures thereof.

In further embodiments, the at least one secondary surfactant is chosen from amphoteric/zwitterionic surfactants, wherein the at least one amphoteric/zwitterionic surfactant is present in a total amount ranging from about 0.1% to about 10% by weight, relative to the total weight of the composition.

In further embodiments, the at least one secondary surfactant is chosen from amphoteric/zwitterionic surfactants, and the at least one amphoteric/zwitterionic surfactant is present in a total amount ranging from about 3% to about 6% by weight, relative to the total weight of the composition.

In further embodiments, the at least one secondary surfactant is chosen from sodium cocoamphoacetate, cocobetaine, cocamidopropyl betaine, coco-glucoside, decyl glucoside, lauryl glucoside, or mixtures thereof.

In further embodiments, the at least one glyceryl ester is chosen from glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, or mixtures thereof.

In further embodiments, the at least one glyceryl ester is glyceryl oleate.

In further embodiments, the at least one glyceryl ester is present in the compositions in an amount ranging from about 0.1% to about 5% by weight, relative to the total weight of the composition.

In further embodiments, the at least one glyceryl ester is present in an amount ranging from about 2% to about 3% by weight, relative to the total weight of the composition.

In further embodiments, the at least one carboxylate anionic surfactant and the at least one glyceryl ester are present in the compositions in a weight ratio ranging from about 0.60 to about 0.90.

In further embodiments, the compositions are substantially free of thickeners.

In some embodiments, the compositions are body cleansing compositions, with the pH ranging from about 7 to about 9. In other embodiments, the compositions are shampoos, and the pH of the compositions ranges from about 4 to about 6.

In further embodiments, the compositions are substantially free of sulfate-based anionic surfactants.

In further embodiments, compositions comprise at least one carboxylate anionic surfactant chosen from disodium cocoyl glutamate, sodium cocoyl glutamate, or mixtures thereof; at least one secondary surfactant, other than the at least one carboxylate anionic surfactant, chosen from sodium cocoamphoacetate, coco-betaine, cocamidopropyl betaine, coco-glucoside, decyl glucoside, lauryl glucoside, or mixtures thereof; the at least one glyceryl ester chosen from glyceryl oleate; and a cosmetically acceptable solvent; and the at least one carboxylate anionic surfactant and the at least one glyceryl ester are present in a weight ratio ranging from about 0.55 to about 0.95, or about 0.60 to about 0.90, or about 0.65 to about 0.85, or about 0.7 to about 0.8.

The disclosed embodiments also relate to methods of cleansing keratin materials. The methods include applying to the keratin material a composition comprising at least one carboxylate anionic surfactant, at least one secondary surfactant other than the at least one carboxylate anionic surfactant, at least one glyceryl ester, and a cosmetically acceptable solvent, wherein the at least one carboxylate anionic surfactant and the at least one glyceryl ester are present in a weight ratio ranging from about 0.50 to about 1.00.

Additional features and advantages of the disclosed embodiments as claimed will be set forth in the detailed description which follows, and in part will be readily apparent to those skilled in the art from that description or recognized by practicing the invention as claimed herein, including the detailed description which follows, as well as the claims.

It is to be understood that both the foregoing general description and the following detailed description present various embodiments of the disclosure, and are intended to provide an overview or framework for understanding the nature and character of the claims.

DETAILED DESCRIPTION OF THE INVENTION

The compositions according to the disclosed embodiments comprise at least one carboxylate anionic surfactant, at least one secondary surfactant other than the at least one carboxylate anionic surfactant, at least one glyceryl ester, and a cosmetically acceptable solvent, wherein the at least one carboxylate anionic surfactant and the at least one glyceryl ester are present in a weight ratio ranging from about 0.50 to about 1.00.

Carboxylate Anionic Surfacants

The compositions according to the disclosed embodiments comprise at least one carboxylate anionic surfactant.

For the purpose of the present disclosure, the term "carboxylate anionic surfactant" means an anionic surfactant comprising one or more carboxylic or carboxylate functions (—COOH or —COO—). They may also optionally comprise one or more sulfonate functions (—SO3H or —SO3-); preferably, however, the carboxylate anionic surfactants according to the present invention do not comprise any sulfonate functions.

The term "anionic surfactant" means a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

In certain embodiments, the carboxylic anionic surfactants that may be used may comprise at least one carboxylic or carboxylate function (—COOH or —COO—).

In certain embodiments, the carboxylate anionic surfactants may be chosen from acylglycinates, acyllactylates, acylsarcosinates, acylglutamates, alkyl-D-galactosideuronic acids, alkyl ether carboxylic acids, alkyl(C6-30 aryl) ether carboxylic acids, alkylamido ether carboxylic acids, or salts thereof.

In certain embodiments, the alkyl and/or acyl groups of these compounds comprise from 6 to 40 carbon atoms, from 6 to 35 carbon atoms, from 6 to 30 carbon atoms, from 6 to 28 carbon atoms, from 6 to 24 carbon atoms, or from 8 to 22 carbon atoms, wherein the alkyl group can be an aryl group (i.e., a phenyl or benzyl group).

In certain embodiments, these compounds are optionally polyoxyalkylenated, and optionally comprise from 1 to 50 ethylene oxide units, or from 2 to 10 ethylene oxide units.

In certain embodiments, the carboxylate anionic surfactants may be chosen from polyglycoside-polycarboxylic acids, including alkyl glucoside citrates, alkyl polyglycoside tartrates, and alkyl polyglycoside sulfosuccinates, alkylsulfosuccinamates, the alkyl group of these compounds comprising from 6 to 40 carbon atoms, or from 6 to 35 carbon atoms, from 6 to 30 carbon atoms, from 6 to 28 carbon atoms, from 6 to 24 carbon atoms, or from 8 to 22 carbon atoms, C6-C40 alkyl monoesters of polyglycoside-polycarboxylic acids, C6-C40 alkyl polyglycoside-citrates, C6-C40 alkyl polyglycoside-tartrates, C6-C40 alkyl polyglycoside-sulfosuccinates, or salts thereof.

In certain embodiments, the carboxylate anionic surfactants may be chosen from polyoxyalkylenated alkyl(amido) ether carboxylic acids or salts thereof, such as those comprising from 2 to 50 alkylene oxide or ethylene oxide groups, such as the compounds sold by the company Kao under the tradename AKYPO.

In certain embodiments, the carboxylate anionic surfactants may be chosen from polyoxyalkylenated alkyl (amido) ether carboxylic acids according to formula (1) below:

wherein:
R$_1$ is chosen from a linear or branched C6-C40 alkyl or alkenyl radical, an alkyl(C8-C9)phenyl radical, or a radical R2CONH—CH2-CH2- wherein R2 is a linear or branched C9-C21 alkyl or alkenyl radical;
n is an integer or decimal number (average value) ranging from 2 to 24, or from 2 to 10;
A is chosen from a hydrogen atom, ammonium, Na, K, Li, Mg, or a monoethanolamine or triethanolamine residue.

In certain embodiments, the carboxylate anionic surfactants are chosen from mixtures of polyoxyalkylenated alkyl (amido) ether carboxylic acids according to formula (1).

In certain embodiments, the polyoxyalkylenated alkyl (amido) ether carboxylic acids according to formula (1) are compounds wherein:
R1 is chosen from a C12-C14 alkyl, cocoyl, oleyl, nonylphenyl, or octylphenyl radical;
A is a hydrogen or sodium atom; and
n is an integer ranging from 2 to 20, or from 2 to 10.

In certain embodiments, the polyoxyalkylenated alkyl (amido) ether carboxylic acids according to formula (1) are compounds wherein R is a C12 alkyl radical, A is a hydrogen or sodium atom, and n ranges from 2 to 10.

In certain embodiments, the salts that may be mentioned may be in the form of alkali metal or alkaline-earth metal, ammonium or amino alcohol salts.

In certain embodiments, when the anionic surfactant is in salt form, the said salt may be chosen from alkali metal salts, including sodium or potassium salt, ammonium salts, amine salts, amino alcohol salts, and alkaline-earth metal salts.

In certain embodiments, the amino alcohol salts may be chosen from monoethanolamine, diethanolamine and triethanolamine salts, monoisopropanolamine, diisopropanolamine or triisopropanolamine salts, 2-am ino-2-methyl-1-propanol salts, 2-amino-2-methyl-1,3-propanediol salts, or tris(hydroxymethyl)aminomethane salts.

In certain embodiments, the compounds may be in the form of alkali metal or alkaline-earth metal salts.

In certain embodiments, the carboxylic anionic surfactants may be chosen from:
acylglutamates, such as C6-C40, or C6-C28, or C6-C24, or C8-C22, especially of C6-C24 or even C12-C20, for example, stearoylglutamates or disodium stearoylglutamate;
acylsarcosinates, such as C6-C40, or C6-C28, or C6-C24, or C8-C22, especially of C6-C24 or even C12-C20, for example, palm itoylsarcosinates or sodium palmitoylsarcosinate;
acyllactylates, such as C6-C40, or C6-C28, or C6-C24, or C8-C22, especially of C12-C28 or even C14-C24, for example, behenoyllactylates or sodium behenoyllactylate;
C6-C40, or C6-C28, or C6-C24, or C8-C22, or C12-C20, acylglycinates;
such as C6-C40, or C6-C28, or C6-C24, or C8-C22, or C12-C20, alkyl ether carboxylates;
polyoxyalkylenated (C6-C40)alkyl(amido) ether carboxylic acids and salts thereof, optionally comprising from 2 to 50 alkylene oxide or ethylene oxide groups, including those in the form of alkali metal or alkaline-earth metal, ammonium or amino alcohol salts; or
mixtures thereof.

In certain embodiments, the carboxylate anionic surfactants may be chosen from acylglycinates, acylsarcosinates, acyllactylates, or acylglutamates, the acyl groups comprising from 6 to 40 carbon atoms, from 6 to 35 carbon atoms, from 6 to 30 carbon atoms, from 6 to 28 carbon atoms, or from 6 to 24 carbon atoms, or from 8 to 22 carbon atoms; or the corresponding salified forms. These compounds may be optionally oxyethylenated and then preferably comprise from 1 to 50 ethylene oxide units, or from 1 to 10 ethylene oxide units.

In certain embodiments, the carboxylate anionic surfactants may be chosen from (C8-C40)acylglutamates, (C8-C40)acylsarcosinates, (C8-C40)acyllactylates, alkyl ether carboxylates, or mixtures thereof, wherein such compounds may be in the form of alkali metal, alkaline-earth metal, ammonium, amine or amino alcohol salts.

In certain embodiments, the at least one carboxylate anionic surfactant is chosen from stearoylglutamates, lauroylglutamates, cocoylglutamates, sodium cocoyl glutamate, disodium cocoyl glutamate, lauryl ether carboxylates, myristoyl glutamate, olivoyl glutamate, capryloyl glutamate, palm itoylsarcosinates, stearoylsarcosinates, lauroylsarcosinates, cocoylacyllactylates, behenoyllactylates, lauroyllactylates, (iso)stearoyllactylates, salts thereof, or mixtures thereof.

In certain embodiments, the at least one carboxylate anionic surfactant may be chosen from disodium cocoylglutamate, sodium cocoyl glutamate, or mixtures thereof.

In an embodiment, the at least one carboxylate anionic surfactant comprises disodium cocoylglutamate and sodium cocoyl glutamate.

The combination of disodium cocoyl glutamate and sodium cocoyl glutamate may be commercially available under the tradename AMISOFT® CS 22, sold by the company Ajinomoto.

In certain embodiments, the at least one carboxylate anionic surfactant may be present in an amount ranging from about 0.1% to about 10% by weight, from about 0.5% to about 7%, from about 0.8% to about 5%, or from about 1% to about 3% by weight, relative to the total weight of the composition. For example, the amount of the at least one carboxylate anionic surfactant is about 0.1%, about 0.2%, about 0.3%, about 0.4%, about 0.5%, about 0.6%, about 0.7%, about 0.8%, about 0.9%, about 1%, 1.5%, about 2%, about 2.5%, about 3%, about 4%, about 5%, about 6%, about 7%, about 8%, about 9%, or about 10% by weight, relative to the total weight of the composition.

Secondary Surfactants

The compositions according to the disclosed embodiments also comprise at least one secondary surfactant that is other than the at least one carboxylate anionic surfactant.

In certain embodiments, the at least one secondary surfactant is chosen from non-carboxylate anionic surfactants, amphoteric/zwitterionic surfactants, nonionic surfactants, or mixtures thereof.

Non-Carboxylate Anionic Surfactants

In certain embodiments, the non-carboxylate anionic surfactants may be chosen from sulfonate anionic surfactants or sulfate anionic surfactants.

In certain embodiments, the sulfonate anionic surfactants comprise at least one sulfonate function (—$SO_3H$ or —$SO_3^-$) and may optionally comprise at least one sulfate function.

In certain embodiments, the sulfonate anionic surfactants comprise at least one sulfonate function (—SO3H or —SO3-).

In certain embodiments, the non-carboxylate anionic surfactants may be chosen from alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates, alkylsulfolaurates, or the salts thereof.

In certain embodiments, the alkyl groups of these compounds comprise from 6 to 40 carbon atoms, from 8 to 35 carbon atoms, from 10 to 30 carbon atoms, from 12 to 28 carbon atoms, from 14 to 24 carbon atoms, or from 16 to 22 carbon atoms; wherein the aryl group is optionally a phenyl or benzyl group.

In certain embodiments, these compounds are optionally polyoxyalkylenated, and optionally comprise from 1 to 50 ethylene oxide units, or from 2 to 10 ethylene oxide units.

In certain embodiments, the sulfonate anionic surfactants may be chosen from:
C6-C24, or C12-C20, alkylsulfosuccinates, for example, laurylsulfosuccinates;
C6-C24, or C12-C20, alkyl ether sulfosuccinates;
C6-C24, or C12-C18, acylisethionates, or
mixtures thereof.

In certain embodiments, the sulfonate anionic surfactants may be in the form of alkali metal or alkaline-earth metal, ammonium or amino alcohol salts.

In certain embodiments, the sulfate anionic surfactants may comprise at least one sulfate function (—OSO3H or —OSO3-).

In certain embodiments, the sulfate anionic surfactants may be chosen from alkyl sulfates, alkyl ether sulfates, alkylamido ether sulfates, alkylaryl polyether sulfates, monoglyceride sulfates, or the salts thereof.

In certain embodiments, the alkyl groups of these compounds comprise from 6 to 40 carbon atoms, from 6 to 35 carbon atoms, from 6 to 30 carbon atoms, from 6 to 28 carbon atoms, or from 6 to 24 carbon atoms; wherein the aryl group is optionally a phenyl or benzyl group.

In certain embodiments, these compounds are optionally polyoxyalkylenated, and optionally comprise from 1 to 50 ethylene oxide units, or from 2 to 10 ethylene oxide units.

In certain embodiments, the sulfate anionic surfactants are chosen from:
alkyl sulfates of C6-C24 or C12-C20;
alkyl ether sulfates of C6-C24 or C12-C20, comprising from 2 to 20 ethylene oxide units.

In certain embodiments, the suflate anionic surfactants may be in the form of alkali metal or alkaline-earth metal, ammonium or amino alcohol salts.

In certain embodiments, the anionic surfactants may be in salt form chosen from alkali metal salts, ammonium salts, amine salts, or alkaline-earth metal salts.

In certain embodiments, the amino alcohol salts may be chosen from monoethanolamine, diethanolamine and triethanolamine salts, monoisopropanolamine, diisopropanolamine or triisopropanolamine salts, 2-am ino-2-methyl-1-propanol salts, 2-amino-2-methyl-1,3-propanediol salts, or tris(hydroxymethyl)aminomethane salts.

In certain embodiments, the anionic surfactants may be chosen from alkali metal or alkaline-earth metal salts.

In certain embodiments, the anionic surfactants may be chosen from:
C6-C24, or C12-C20, alkyl sulfates;
C6-C24, or C12-C20, alkyl ether sulfates, optionally comprising from 2 to 20 ethylene oxide units;
C6-C24, or C12-C20, alkylsulfosuccinates, for example, laurylsulfosuccinates;
C6-C24, or C12-C20, alkyl ether sulfosuccinates; or
C6-C24, or from C12-C18, acylisethionates.

In certain embodiments, the anionic surfactants above may be in the form of alkali metal or alkaline-earth metal, ammonium or amino alcohol salts.

In certain embodiments, the anionic surfactants may be sulfate anionic surfactants chosen from:
C6-C24, or C12-C20, alkyl sulfates;
C6-C24, or C12-C20, alkyl ether sulfates, optionally comprising from 2 to 20 ethylene oxide units.

In certain embodiments, the sulfate anionic surfactants above may be in the form of alkali metal or alkaline-earth metal, ammonium or amino alcohol salts.

In certain embodiments, the non-carboxylate anionic surfactants may be chosen from sulfate anionic surfactants such as sodium lauryl sulfate, sodium laureth sulfate, or mixtures thereof.

Amphoteric/Zwitterionic Surfactants

In certain embodiments, the secondary surfactant may be chosen from amphoteric/zwitterionic surfactants.

In certain embodiments, the amphoteric/zwitterionic surfactants may be chosen from betaines, sultaines, amphoacetates, amphoproprionates, or mixtures thereof. In other embodiments, amphoteric/zwitterionic surfactants may be chosen from compounds according to the formulas below:

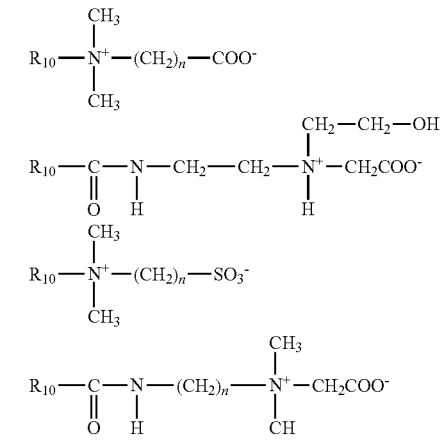

wherein:

R$^{10}$ is an alkyl group having 6-24 carbon atoms; and n is an integer from 1 to 3.

In certain embodiments, the amphoteric/zwitterionic surfactants may be chosen from coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, or mixtures thereof.

In certain embodiments, the amphoteric/zwitterionic surfactants include betaines which may be chosen from coco betaine, cocoamidopropyl betaine, behenyl betaine, capryl/capramidopropyl betaine, lauryl betaine, or mixtures thereof.

In certain embodiments, the betaines may be chosen from coco betaine or cocoamidopropyl betaine.

In certain embodiments, the hydroxyl sultaines may be chosen from compounds according to the formula below:

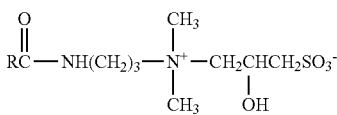

wherein R is an alkyl group having 6-24 carbon atoms.

In certain embodiments, the amphoacetates may include alkylamphoacetates chosen from compounds according to the formula below:

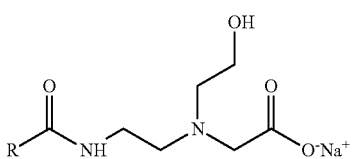

wherein R is an alkyl group having 6-24 carbon atoms.

In certain embodiments, the amphoacetates may include alkyl amphodiacetates chosen from compounds according to the formula below:

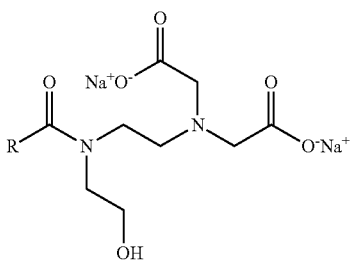

wherein R is an alkyl group having 6-24 carbon atoms.

In certain embodiments, the amphoteric/zwitterionic surfactants may be chosen from optionally quaternized secondary or tertiary aliphatic amine derivatives, wherein the aliphatic group is a linear or branched chain comprising from 8 to 22 carbon atoms, the amine derivatives containing at least one anionic group, wherein the at least one anionic group may be chosen from a carboxylate, sulfonate, sulfate, phosphate or phosphonate group.

In certain embodiments, the amphoteric/zwitterionic surfactants may be chosen from (C$_8$-C$_{20}$)alkylbetaines, (C$_8$-C$_{20}$)alkylamido (C$_1$-C$_6$)alkylbetaines, sulfobetaines, (C$_8$-C$_{20}$)alkylsulfobetaines, (C$_8$-C$_{20}$)alkylamido(C$_1$-C$_6$) alkylsulfobetaines, (C$_8$-C$_{20}$)alkylamphoacetate, (C$_8$-C$_{20}$) alkylamphodiacetate, salts thereof, or mixtures thereof.

In certain embodiments, the optionally quaternized secondary or tertiary aliphatic amine derivatives that may be chosen from compounds according to formulas (A1) and (A2) below:

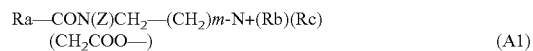

$$Ra—CON(Z)CH_2—(CH_2)m-N+(Rb)(Rc) \\ (CH_2COO—) \qquad (A1)$$

wherein:

Ra is chosen from a C$_{10}$-C$_{30}$ alkyl or alkenyl group derived from an acid Ra—COOH, present in hydrolysed coconut oil, a heptyl group, a nonyl group, or an undecyl group;

Rb is a β-hydroxyethyl group;

Rc is a carboxymethyl group;

m is equal to 0, 1, or 2; and

Z is chosen from a hydrogen atom or a hydroxyethyl or carboxymethyl group,

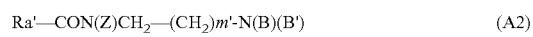

$$Ra'—CON(Z)CH_2—(CH_2)m'-N(B)(B') \qquad (A2)$$

wherein:

B is a —CH$_2$CH$_2$OX' group, wherein X' is chosen from —CH$_2$—COOH, CH$_2$—COOZ', CH$_2$CH$_2$—COOH, —CH$_2$CH$_2$—COOZ', or a hydrogen atom;

B' is —(CH$_2$)z-Y' group, wherein z=1 or 2, and Y' is chosen from COOH, COOZ', CH$_2$—CHOH—SO$_3$H, or —CH$_2$—CHOH—SO$_3$Z', m' is equal to 0, 1, or 2;

Z is chosen from a hydrogen atom or a hydroxyethyl or carboxymethyl group;

Z' is an ion resulting from an alkali or alkaline-earth metal, an ammonium ion, or an ion resulting from an organic amine; and Ra' is chosen from a C$_{10}$-C$_{30}$ alkyl or alkenyl group of an acid Ra'COOH optionally pre-sent in hydrolysed linseed oil or coconut oil, an alkyl group, or an unsaturated C$_{17}$ group.

In certain embodiments, the compounds according to formula (A2) may be chosen from sodium cocoamphoacetate, sodium lauroamphoacetate, sodium caproamphoacetate, or sodium capryloamphoacetate.

In certain embodiments, the compounds according to formula (A2) may be chosen from disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid, or cocoamphodipropionic acid.

Examples that may be mentioned include sodium cocoamphodiacetate sold under the tradename Miranol® C2M Concentrate by the company Rhodia, sodium cocoamphoacetate sold under the tradename Miranol® Ultra C 32 by the company Rhodia or under the tradename REWOTERIC® AM C KL by the company Evonik Goldschmidt and the product sold by the company Chimex under the tradename CHIMEXANE HA.

In certain embodiments, the amphoteric/zwitterionic surfactant may be chosen from compounds according to formula (A3) below:

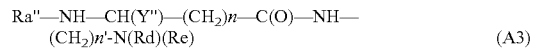

$$Ra"—NH—CH(Y")—(CH_2)n—C(O)—NH— \\ (CH_2)n'-N(Rd)(Re) \qquad (A3)$$

wherein:

Ra" is chosen from a C10-C30 alkyl or alkenyl group of an acid Ra"—C(O)OH, optionally present in hydrolysed linseed oil or coconut oil;

Y″ is chosen from a —C(O)OH, —C(O)OZ″, —CH$_2$—CH(OH)—SO$_3$H, or CH$_2$—CH(OH)—SO$_3$—Z″ group, wherein Z″ is chosen from a cationic counterion resulting from an alkali metal or alkaline-earth metal, an ammonium ion, or an ion resulting from an organic amine;

Rd and Re are, independently of each other, chosen from a C$_1$-C$_4$ alkyl or hydroxyalkyl radical; and n and n′ are, independently of each other, an integer ranging from 1 to 3.

In certain embodiments, the compounds corresponding to formula (A3) may be chosen from sodium diethylaminopropylcocoaspartamide.

In certain embodiments, the amphoteric/zwitterionic surfactant may be chosen from coco-betaine, cocamidopropylbetaine, sodium cocoamphoacetate, disodium cocoamphodiacetate, or mixtures thereof.

Nonionic Surfactants

In certain embodiments, the nonionic surfactants may be chosen from alcohols, α-diols and (C1-20)alkylphenols, these compounds being polyethoxylated, polypropoxylated or bearing a fatty chain comprising, for example, from 8 to 40 carbon atoms or from 16 to 30 carbon atoms, the number of ethylene oxide and/or propylene oxide groups ranging from 2 to 50, and the number of glycerol groups ranging from 2 to 30.

In certain embodiments, the nonionic surfactants may be chosen from condensates of ethylene oxide and of propylene oxide with fatty alcohols, polyethoxylated fatty amides preferably having from 2 to 30 ethylene oxide units, polyglycerolated fatty amides containing about 1 to 5, or 1.5 to 4, glycerol groups, ethoxylated fatty acid esters of sorbitan preferably containing from 2 to 40 ethylene oxide units, fatty acid esters of sucrose, fatty acid esters of polyethylene glycol, N—(C6-24 alkyl)glucamine derivatives, or amine oxides, for example, (C10-14alkyl)amine oxides or N—(C10-14 acyl)aminopropylmorpholine oxides.

In certain embodiments, the nonionic surfactants may be chosen from ethoxylated fatty acid esters of sorbitan and polyethoxylated fatty alcohols, or mixtures thereof.

In certain embodiments, the nonionic surfactants may be chosen from nonionic surfactants of alkylpolyglycoside (also called alkylpolyglucoside) type chosen from compounds according to the formula below:

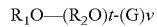

R$_1$O—(R$_2$O)t-(G)v wherein:

R$_1$ is chosen from a linear or branched alkyl or alkenyl radical comprising 6 to 24 carbon atoms, or 8 to 18 carbon atoms, or an alkylphenyl radical whose linear or branched alkyl radical comprises 6 to 24 carbon atoms, or 8 to 18 carbon atoms;

R$_2$ is chosen from an alkylene radical comprising 2 to 4 carbon atoms;

G is a sugar unit comprising 5 to 6 carbon atoms;

t is a value ranging from 0 to, 10, or from 0 to 4; and v is a value ranging from 1 to 15 or 1 to 4.

In certain embodiments, the alkylpolyglycoside surfactants may be chosen from compounds according to the formula described above in which R$_1$ is chosen from a saturated or unsaturated, linear or branched alkyl radical comprising from 8 to 18 carbon atoms; t is a value ranging from 0 to 3, or equal to 0; G is chosen from glucose, fructose or galactose; and the degree of polymerization, i.e. the value of v, may range from 1 to 15, or from 1 to 4, or from 1 to 2.

In certain embodiments, the glucoside bonds between the sugar units are generally of 1-6 or 1-4 type.

In certain embodiments, the nonionic surfactants may be chosen from commercial products sold under the PLANTACARE tradenames by the company BASF, including lauryl glucoside (PLANTACARE® 1200 UP or UP/MB), decyl glucoside, (PLANTACARE® 2000 UP or UP/MB), or coco-glucoside (PLANTACARE® 818 UP or UP/MB).

In certain embodiments, the nonionic surfactants are chosen from coco-glucoside, commercially available under the tradename PLANTACARE® 818/UP by BASF.

In certain embodiments, the at least secondary surfactant is chosen from sodium cocoamphoacetate, coco-glucoside, coco-betaine, or mixtures thereof.

In certain embodiments, the at least one secondary surfactant is present in a total amount ranging from about 0.1% to about 25% by weight, from about 1% to about 22% by weight, from about 2% to about 20% by weight, or from about 3% to about 18% by weight, relative to the total weight of the composition. According to certain embodiments, the amount of the at least one secondary surfactant is about 0.1%, about 0.5%, about 1%, about 1.5%, about 2%, about 2.5%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight, relative to the total weight of the composition.

In certain embodiments, wherein the at least one secondary surfactant is chosen from nonionic surfactants, the at least one nonionic surfactant is present in an amount ranging from about 0.1% to about 20% by weight, e.g., from about 0.5% to about 19% by weight, from about 1% to about 18% by weight, from about 2% to about 17% by weight, from about 3% to about 16% by weight, from about 4% to about 14% by weight, or from about 8% to about 12% by weight, relative to the total weight of the composition. According to certain embodiments, the amount of the at least one nonionic surfactant is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, relative to the total weight of the composition.

In certain embodiments, wherein the at least one secondary surfactant is chosen from amphoteric/zwitterionic surfactants, the at least one amphoteric/zwitterionic surfactant is present in an amount ranging from about 0.1% to about 10% by weight, for example, from about 0.5% to about 9% by weight, from about 1% to about 8% by weight, from about 2% to about 7% by weight, or from about 3% to about 6% by weight, relative to the total weight of the composition. According to certain emodiments, the amount of the at least one amphoteric/zwitterionic surfactant is about 0.1%, about 0.5%, about 1%, about 2%, about 3%, about 4%, about 5%, about 6%, about 7%, about 8%, about 9%, or about 10% by weight, relative to the total weight of the composition.

Glyceryl Esters

The compositions according to the disclosed embodiments further comprise at least one glyceryl ester.

In certain embodiments, the at least one glyceryl ester (or (poly)glyceryl ester) may be chosen from glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, or mixtures thereof. In certain embodiments, the at least one glyceryl ester may be chosen from polyglyceryl-4 isostearate, polyglyceryl-3 oleate, polyglyceryl-2 sesquioleate, triglyceryl diisostearate, diglyceryl monooleate, tetraglyceryl monooleate, or mixtures thereof.

In certain embodiments, the at least one glyceryl ester may be chosen from polyglyceryl-3 caprate, polyglyceryl-4 caprate, glyceryl laurate, polyglyceryl-2 laurate, polyglyceryl-5 laurate, polyglyceryl-10 laurate, glyceryl myristate, glyceryl stearate, glyceryl undecylenate, glyceryl oleate, or mixtures thereof.

In certain embodiments, the at least one glyceryl ester may be chosen from glyceryl oleate.

In certain embodiments, the at least one glyceryl ester may be present in an amount ranging from about 0.1% to about 5% by weight, or from about 2% to about 3% by weight, relative to the total weight of the composition.

In certain embodiments, the at least one glyceryl ester may be present in an amount of about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, or about 5% by weight, relative to the total weight of the composition.

In certain embodiments, the at least one carboxylate anionic surfactant and the at least one glyceryl ester are present in the compositions in a weight ratio ranging from about 0.50 to about 1.00, or from about 0.60 to about 0.90, including ranges and sub-ranges therebetween. In certain embodiments, the ratio of the least one carboxylate anionic surfactant to the at least one glyceryl ester is about 0.50, about 0.55, about 0.60, about 0.65, about 0.70, about 0.75, about 0.80, about 0.85, about 0.90, about 0.95, or about 1.00.

Cosmetically Acceptable Solvents

The compositions according to the disclosed embodiments comprise at one cosmetically acceptable solvent.

In certain embodiments, the cosmetically acceptable solvents may be chosen from organic solvents, water-soluble solvents, or water.

In certain embodiments, the cosmetically acceptable solvents may be chosen from organic solvents, such as C1-4 alcohols, polyols, glycols, or mixtures thereof. In certain embodiments, the organic solvents may be chosen from monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In certain embodiments, the cosmetically acceptable solvents may be chosen from polyols, which may include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In certain embodiments, the cosmetically acceptable solvents may be chosen from polyhydric alcohols, which may include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, or mixtures thereof.

In certain embodiments, the cosmetically acceptable solvents may be chosen from polyol compounds, which may include aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, or mixtures thereof.

In certain embodiments, the cosmetically acceptable solvents may be chosen from glycols, C1-4 alcohols, polyols, or mixtures thereof. In certain embodiments, the cosmetically acceptable solvents may be chosen from hexylene glycol, propylene glycol, caprylyl glycol, glycerin, ethanol, isopropyl alcohol, or mixtures thereof.

In certain embodiments, the cosmetically acceptable solvents are present in an amount ranging from about 0.1% to about 25% by weight, from about 0.1% to about 20% by weight, from about 0.1% to about 15% by weight, from about 0.1% to about 10% by weight, from about 0.5% to about 20% by weight, from about 0.5% to about 15% by weight, from about 0.5% to about 10% by weight, from about 2% to about 20% by weight, from about 2% to about 15% by weight, from about 5% to about 20% by weight, or from about 5% to about 15% by weight, relative to the total weight of the composition.

In certain embodiments, water is present in present in an amount ranging from about 50% to about 95% by weight, from about 60% to about 90% by weight, from about 50% to about 85% by weight, or from about 60% to about 85% by weight, relative to the total weight of the composition.

Emulsifiers

In certain embodiments, the compositions may include additional emulsifiers other than the glyceryl esters described above. The emulsifiers may be chosen from fatty acids, fatty alcohols, esters of polyols and of a fatty acid, polyol fatty esters and fatty ethers with a branched or unsaturated chain containing from 10 to 30 carbon atoms, esters of sugar and of a fatty acid, or mixtures thereof. The fatty chains in the emulsifiers may be, for example, from about 8 to about 35 carbon atoms in length, and may be saturated or unsaturated, and may be optionally branched. In certain embodiments, the fatty chains are about 10 to about 30 carbon atoms in length or about 12 to about 24 carbon atoms in length.

In certain embodiments, the emulsifiers may be glycol esters chosen from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, or mixtures thereof.

PH Adjusters

The composition may also contain pH adjusters chosen from acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

In certain embodiments, the pH adjusters may be chosen from citric acid or sodium hydroxide.

In certain embodiments, the pH adjusters may be citric acid.

In certain embodiments, the pH adjusters may be present in an amount ranging from about 0.01% to about 3% by weight, or from about 0.1% to about 2% by weight, relative to the total weight of the composition.

In certain embodiments, the pH of the composition may range from about 4 to about 9. In certain embodiments, the pH of the composition may range from about 7 to about 6.

The compositions according to the invention may additionally comprise cosmetic adjuvants chosen from fragrances, pigments, chelating agents, softeners, antioxidants, opacifiers, stabilizers, moisturizing agents, vitamins, bactericides, preservatives, polymers, thickening agents, or any other ingredient commonly used in cosmetics for this type of application.

In certain embodiments, the compositions are substantially free of thickeners.

Of course, a person skilled in the art will take care to choose such optional additional compounds so that the advantageous properties intrinsically attached to the composition in accordance with the invention are not, or not substantially, detrimentally affected by the envisaged addition or additions.

The amounts of these various constituents which can be present in the composition according to the invention are those conventionally used in the art. The composition according to the invention especially finds a particularly advantageous application in the hair sector, especially for caring for, and/or cleansing the hair or the scalp. The hair compositions are preferably shampoos, hair conditioners, styling or care gels, care lotions or creams, conditioners, masks, sera, lotions or shampoos for combating hair loss, antiparasitic shampoos, antidandruff lotions or shampoos, or shampoos for treating seborrhoea. Preferably, the composition according to the invention is a shampoo.

The composition according to the invention may be contained in a tube, in a bottle optionally equipped with a pump, or alternatively in an aerosol. In the case of an aerosol, the composition may then contain one or more standard propellants.

Advantageously, the composition according to the invention is in the form of a hair composition for cleansing the hair; preferentially, the composition according to the invention is a shampoo.

A subject of the invention is also a treatment process or method, especially for caring for, cleansing and/or conditioning keratin materials, especially the hair and/or the scalp, comprising the application to the said materials of a composition according to the invention.

It is in particular a hair treatment process or method, for caring for, cosmetically treating and/or cleansing the hair and/or the scalp.

The following examples serve to illustrate the invention without however exhibiting a limiting character. In these examples the amounts of the composition ingredients are given as weight percentages relative to the total weight of the composition.

EXAMPLES

TABLE 1

| Ingredients | Example 1 | Example 2 | Example 3 | Comparative Example 4 (Reference Product) |
|---|---|---|---|---|
| Disodium cocoyl glutamate and/or sodium cocoyl glutamate | 1.75 | 2.00 | 2.25 | |
| Glyceryl oleate | 2.50 | 2.50 | 2.80 | 2.00 |
| Coco-glucoside | 4.00 | 9.88 | 10.40 | |
| Sodium cocoamphoacetate | | 2.56 | | |
| Coco-betaine | | 1.80 | 4.50 | |
| Thickeners (e.g., sclerotium gum, xanthan gum, hydroxypropyl guar hydroxypropyltrimonium chloride) | | | | 1.30 |
| Sodium lauroyl methyl isethionate | | | | 3.35 |
| Sodium lauroyl sarcosinate | | | | 0.06 |
| Decyl glucoside | | | | 7.80 |
| Cocamide MIPA | | | | 1.00 |
| pH adjuster (e.g., citric acid, etc.) | 1.00 | 0.80 | 0.50 | 0.25 |
| Additional components (e.g., conditioners, preservatives, cleansing agents, emulsifiers, etc.) | 1.65 | 1.70 | 1.68 | 1.57 |
| Fatty compounds (e.g., seed oil, lecithin, *cocos nucifera* fruit extract, hydrogenated palm glycerides citrate) | | | | 0.01 |
| Water | Q.S. to 100 | Q.S. to 100 | Q.S. to 100 | Q.S. to 100 |

The viscosities of the compositions were measured using the Ford Cup to capture a total of 90 g sample flowing through an opening diameter of 6 mm at 25° C. The viscosity of the inventive compositions fell in the range of 50-70 seconds. The inventive compositions did not contain conventional thickener(s). The viscosity of the comparative formula fells in the range of 70-120 seconds.

A shampoo according to Example 1 was tested and compared to the Reference Product (Example 4) on 10 volunteers by applying the shampoo of Example 1 to hair on half of the volunteer's head and Example 4 on the other half of the head, lathering, rinsing, and then blow drying the hair. The composition of Example 1 produced a foam that was more airy. The foam was also easier to rinse from the hair. It also left the hair feeling cleaner (more squeaky clean), better individualized, and less coated, compared to the Reference Product, which contained polymer thickeners.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All percentages, parts and ratios herein are based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. The compositions of the disclosure may be free of the component(s) or may be "substantially free" or "essentially free" of the component(s) described for optional inclusion in said compositions. Nonetheless, the compositions may include less than about 1 wt. %, less than about 0.5 wt. %, less than about 0.1 wt. %, or none of the specified material or components.

Unless otherwise expressly stated, it is in no way intended that any method set forth herein be construed as requiring that its steps be performed in a specific order. Accordingly, where a method claim does not expressly recite an order to be followed by its steps or it is not otherwise specifically stated in the claims or descriptions that the steps are to be limited to a specific order, it is no way intended that any particular order be inferred.

The invention claimed is:

1. A composition comprising:
   at least one carboxylate anionic surfactant, wherein the at least one carboxylate anionic surfactant is selected from stearoylglutamates, lauroylglutamates, or cocoylglutamates, or mixtures thereof;
   at least one secondary surfactant other than the at least one carboxylate anionic surfactant;
   at least one glyceryl ester, wherein the at least one glyceryl ester is selected from glyceryl laurate, glyceryl myristate, glyceryl stearate, glyceryl undecylenate, glyceryl oleate, or mixtures thereof; and
   a cosmetically acceptable solvent;
   wherein the at least one carboxylate anionic surfactant and the at least one glyceryl ester are present in a weight ratio ranging from 0.50 to about 1.00.

2. The composition of claim 1, wherein the at least one carboxylate anionic surfactant is chosen from disodium cocoyl glutamate, sodium cocoyl glutamate, or mixtures thereof.

3. The composition of claim 1, wherein the at least one carboxylate anionic surfactant is present in a total amount ranging from about 0.1% to about 10% by weight, relative to the total weight of the composition.

4. The composition of claim 1, wherein the at least one carboxylate anionic surfactant is present in a total amount ranging from about 1% to about 3% by weight, relative to the total weight of the composition.

5. The composition of claim 1, wherein the at least one secondary surfactant is chosen from non-carboxylate anionic surfactants, amphoteric/zwitterionic surfactants, nonionic surfactants, or mixtures thereof.

6. The composition of claim 1, wherein the at least one secondary surfactant is present in a total amount ranging from about 0.1% to about 25% by weight, relative to the total weight of the composition.

7. The composition of claim 1, wherein the at least one secondary surfactant is present in a total amount ranging from about 3% to about 18% by weight, relative to the total weight of the composition.

8. The composition of claim 1, wherein the at least one secondary surfactant is chosen from nonionic surfactants chosen from lauryl glucoside, decyl glucoside, coco-glucoside, or mixtures thereof.

9. The composition of claim 8, wherein the at least one nonionic surfactant is present in a total amount ranging from about 0.1% to about 20% by weight, relative to the total weight of the composition.

10. The composition of claim 9, wherein the at least one nonionic surfactant is present in a total amount ranging from about 8% to about 12% by weight, relative to the total weight of the composition.

11. The composition of claim 1, wherein the at least one secondary surfactant is chosen from amphoteric/zwitterionic surfactants chosen from betaines, sultaines, amphoacetates, amphoproprionates, or mixtures thereof.

12. The composition of claim 11, wherein the at least one amphoteric/zwitterionic surfactant is present in a total amount ranging from about 0.1% to about 10% by weight, relative to the total weight of the composition.

13. The composition of claim 12, wherein the at least one amphoteric/zwitterionic surfactant is present in a total amount ranging from about 3% to about 6% by weight, relative to the total weight of the composition.

14. The composition of claim 1, wherein the at least one secondary surfactant is chosen from sodium cocoamphoacetate, coco-betaine, cocamidopropyl betaine, coco-glucoside, decyl glucoside, lauryl glucoside, or mixtures thereof.

15. The composition of claim 1, wherein the at least one glyceryl ester is glyceryl oleate.

16. The composition of claim 1, wherein the at least one glyceryl ester is present in an amount ranging from about 0.1% to about 5% by weight, relative to the total weight of the composition.

17. The composition of claim 16, wherein the at least one glyceryl ester is present in an amount ranging from about 2% to about 3% by weight, relative to the total weight of the composition.

18. The composition of claim 1, wherein the at least one carboxylate anionic surfactant and the at least one glyceryl ester are present in a weight ratio ranging from about 0.60 to about 0.90.

19. The composition of claim 1, wherein the composition is substantially free of thickeners.

20. The composition of claim 1, wherein the composition is a body cleansing composition, wherein the pH of the composition ranges from about 7 to about 9.

21. The composition of claim 1, wherein the composition is a shampoo, wherein the pH of the composition ranges from about 4 to about 6.

22. The composition of claim 1, wherein the composition is substantially free of sulfate-based anionic surfactants.

23. A composition comprising:
- at least one carboxylate anionic surfactant chosen from disodium cocoyl glutamate, sodium cocoyl glutamate, or mixtures thereof;
- at least one secondary surfactant, other than the at least one carboxylate anionic surfactant, chosen from sodium cocoamphoacetate, coco-betaine, cocamidopropyl betaine, coco-glucoside, decyl glucoside, lauryl glucoside, or mixtures thereof;
- at least one glyceryl ester chosen from glyceryl oleate; and
- a cosmetically acceptable solvent;
- wherein the at least one carboxylate anionic surfactant and the at least one glyceryl ester are present in a weight ratio ranging from 0.5 to about 1.00.

24. A method of cleansing keratin materials, comprising applying to the keratin materials a composition, the composition comprising:
- at least one carboxylate anionic surfactant, wherein the at least one carboxylate anionic surfactant is selected from stearoylglutamates, lauroylglutamates, or cocoylglutamates, or mixtures thereof;
- at least one secondary surfactant other than the at least one carboxylate anionic surfactant;
- at least one glyceryl ester, wherein the at least one glyceryl ester is selected from glyceryl laurate, glyceryl myristate, glyceryl stearate, glyceryl undecylenate, glyceryl oleate, or mixtures thereof; and
- a cosmetically acceptable solvent;
- wherein the at least one carboxylate anionic surfactant and the at least one glyceryl ester are present in a weight ratio ranging from 0.50 to about 1.00.

* * * * *